US012605057B2

(12) United States Patent
    Arcand et al.

(10) Patent No.:  US 12,605,057 B2
(45) Date of Patent:       Apr. 21, 2026

(54) LIGHTED SPECULUM

(71) Applicant: Glimpse Diagnostics, Inc.,
               Minneapolis, MN (US)

(72) Inventors: Ben Arcand, Minneapolis, MN (US);
               Courtney Anne Hill, Arden Hills, MN
               (US)

(73) Assignee: Glimpse Diagnostics, Inc.,
               Minneapolis, MN (US)

( * ) Notice:   Subject to any disclaimer, the term of this
               patent is extended or adjusted under 35
               U.S.C. 154(b) by 5 days.

(21) Appl. No.: 18/775,502

(22) Filed:     Jul. 17, 2024

(65)            Prior Publication Data

US 2025/0025034 A1       Jan. 23, 2025

Related U.S. Application Data

(60) Provisional application No. 63/514,853, filed on Jul.
     21, 2023.

(51) Int. Cl.
     *A61B 1/06*          (2006.01)
     *A61B 1/227*         (2006.01)
(52) U.S. Cl.
     CPC ............ *A61B 1/227* (2013.01); *A61B 1/0676*
                   (2013.01); *A61B 1/0684* (2013.01)
(58) Field of Classification Search
     CPC ....... A61B 1/0676; A61B 1/0684; A61B 1/24;
                            A61B 1/227; A61B 1/233
     See application file for complete search history.

(56)              References Cited

U.S. PATENT DOCUMENTS

|  | | | | |
|---|---|---|---|---|
| 3,146,775 | A  * | 9/1964 | Moore ................... | A61B 1/227 |
| | | | | 385/115 |
| 3,374,791 | A  * | 3/1968 | Westerman ............ | A61B 1/227 |
| | | | | 600/184 |
| 3,384,076 | A  * | 5/1968 | Speelman .............. | A61B 1/227 |
| | | | | 385/115 |
| 3,698,387 | A  * | 10/1972 | Moore ................. | A61B 1/2275 |
| | | | | 385/115 |
| 3,728,998 | A  * | 4/1973 | Heine ................... | A61B 1/227 |
| | | | | 385/117 |
| 4,991,069 | A  * | 2/1991 | Tiller ................. | A61B 1/00034 |
| | | | | 362/183 |
| 5,785,648 | A  * | 7/1998 | Min ......................... | A61B 1/32 |
| | | | | 600/206 |
| 10,405,844 | B2 * | 9/2019 | Wan ..................... | A61B 1/0676 |
| 2003/0187331 | A1 * | 10/2003 | Faludi .................. | A61B 1/0676 |
| | | | | 600/200 |
| 2004/0186352 | A1 * | 9/2004 | Roberts .................. | A61B 1/227 |
| | | | | 600/179 |
| 2013/0267783 | A1 * | 10/2013 | Davis ..................... | A61B 1/227 |
| | | | | 600/199 |
| 2024/0315544 | A1 * | 9/2024 | Un ......................... | A61B 1/042 |

* cited by examiner

*Primary Examiner* — Nicholas W Woodall
(74) *Attorney, Agent, or Firm* — Fredrikson & Byron,
P.A.

(57)              ABSTRACT

An otoscope speculum includes a body having a neck and a
stopper portion, a cap having a flange overhang and a flat
distal face, a channel having a proximal opening in the cap
and a distal opening in the neck, and at least one light
embedded within the neck. A length of the body can be
defined by a first axis. A length of the cap can be defined by
a second axis, and a height of the cap can be defined by the
first axis. The at least one light may be completely embedded
near the distal tip of the neck.

21 Claims, 7 Drawing Sheets

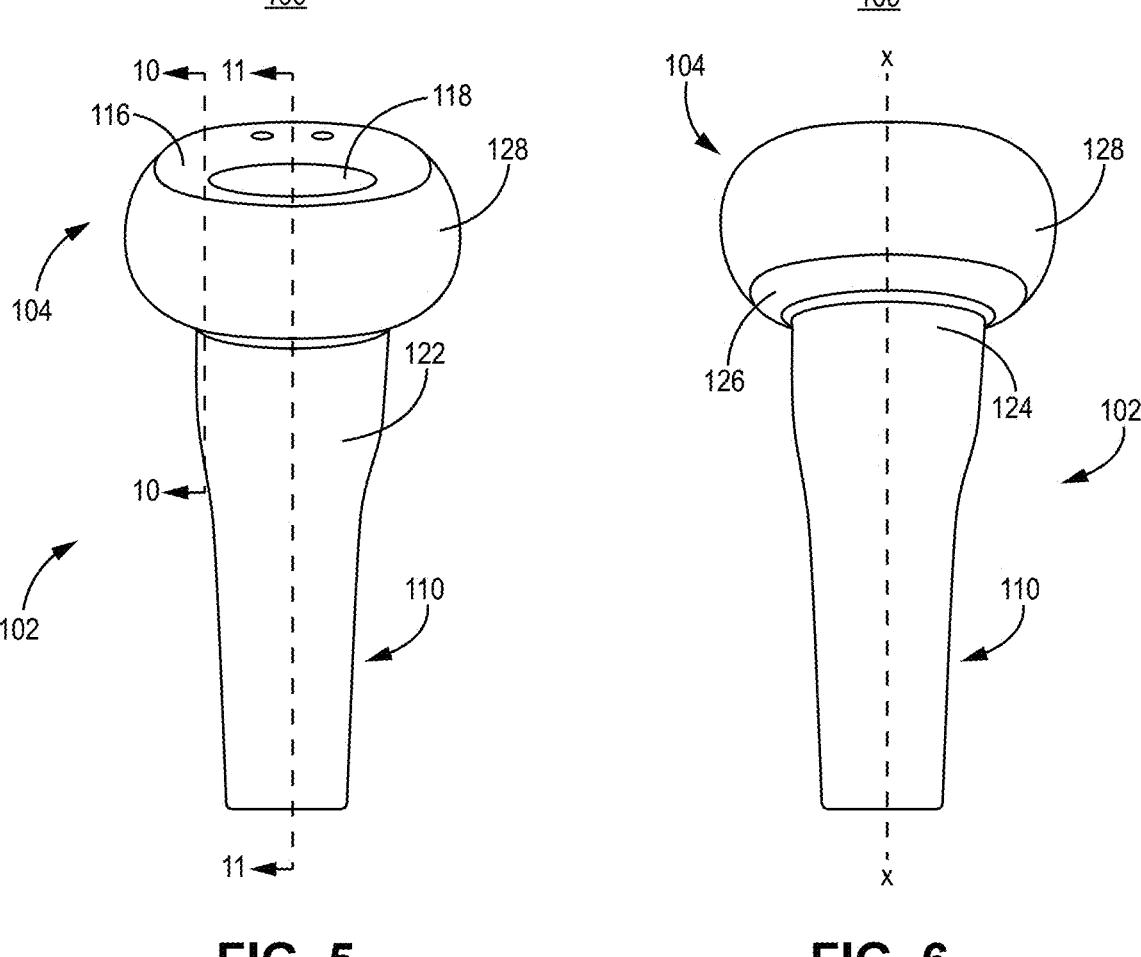
FIG. 5        FIG. 6

LIGHTED SPECULUM

RELATED APPLICATION

This application claims priority to U.S. Provisional Patent Application No. 63/514,853, filed Jul. 21, 2023, the contents of which are hereby incorporated by reference.

FIELD OF THE INVENTION

This disclosure relates to a lighted speculum. More specifically, it relates to a speculum having a lighted tip that can be used in combination with an otoscope to diagnose inner ear conditions.

BACKGROUND OF THE INVENTION

Telemedicine has become considerably more common in recent history. However, certain aspects of medicine, such as diagnosis of conditions or diseases, can be difficult to accomplish remotely and have continued to occur in clinics or at other medical practice facilities. One such example is diagnosis of inner ear conditions, which is an especially common occurrence in children. Despite the frequency with which children must often see a medical professional for inner ear diagnoses, and the disruption those visits have on parents' lives, no useful tools have been created or marketed to parents to enable them to take advantage of expanding telemedicine for these purposes. Therefore, a tool and system is needed that can expand telemedicine offerings to parents whose children suffer from potential inner ear conditions.

SUMMARY OF THE INVENTION

The present disclosure relates to an otoscope speculum having a lighted tip. In an illustrative but non-limiting example, the disclosure provides an otoscope speculum that can include a body having a neck and a stopper portion, a cap having a flange overhang and a flat distal face, a channel having a proximal opening in the cap and a distal opening in the neck, and at least one light embedded within the neck. A length of the body can be defined by a first axis. A length of the cap can be defined by a second axis, and a height of the cap can be defined by the first axis. In some cases, the body and the cap can be comprised of a clear silicone.

In some cases, the at least one light can be completely embedded near the distal tip of the neck. Additionally, the at least one light can be comprised of two light emitting diodes positioned adjacent to each other. Further, the two light emitting diodes can be located on a posterior portion of the neck. Alternatively, the at least one light can be comprised of at least four light emitting diodes positioned circumferentially around the distal tip of the neck. In some cases, the at least one light can be aligned between a parallel position to the first axis of the body and a 30-degree angle toward a central axis of the channel. In yet other cases, the at least one light can be either a fiber optic cable or a light pipe, and the at least one light can have an emitting end near the distal tip of the neck.

In some cases, the neck can be approximately cylindrical. In some cases, the stopper portion can include an anterior bump to aid in aligning the otoscope speculum in the car. Further, the stopper portion can also include a posterior bump that has a shorter height than a height of the anterior bump.

In some cases, the otoscope speculum can be combined with an otoscope. The otoscope can include a switch, such as a reed or hall effect switch, and the combination of the otoscope with the otoscope speculum can activate the switch, which can activate the at least one light.

In some cases, the at least one light can be connected to a circuit board that is embedded within the otoscope speculum. Further, the circuit board can be embedded within the flange of the cap. Additionally, the circuit board includes a switch, and the switch can be one of a reed or hall effect switch. In some cases, the otoscope speculum can be combined with an otoscope, and the switch can be activatable by a component in the channel. In some cases, the circuit board can interface with a battery, and the battery can be embedded within the flange of the cap. The circuit board may further include a current limiting diode.

In some cases, the cap of the otoscope speculum can be approximately cylindrical, and the height of the cap can be less than the length of the cap. In some cases, the at least one light has a built-in lens having a beam range of up to 120 degrees. More specifically, the beam range can be 45-60 degrees.

BRIEF DESCRIPTION OF THE DRAWINGS

FIG. 5 is a front view of the otoscope speculum.

FIG. 6 is a rear view of the otoscope speculum.

DETAILED DESCRIPTION

Figure 1:
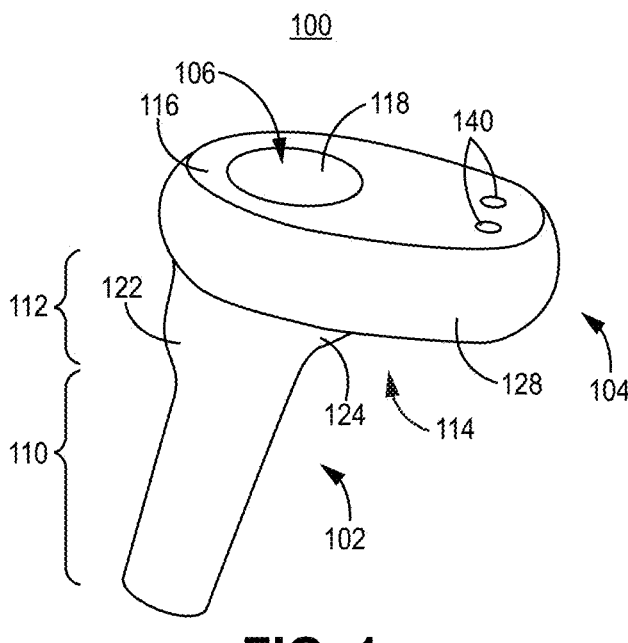
FIG. 1 is a side perspective view of an otoscope speculum.

The present disclosure relates to an otoscope speculum having a lighted tip that can be used in combination with an otoscope to diagnose inner ear conditions. Various embodiments of the otoscope speculum will be described in detail with reference to the drawings, wherein like reference numerals represent like parts and assemblies throughout the several views. Reference to various embodiments does not limit the scope of the otoscope speculum disclosed herein. Additionally, any examples set forth in this specification are not intended to be limiting and merely set forth some of the many possible embodiments for the otoscope speculum. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

Some embodiments of the otoscope speculum disclosed herein include features that enable the otoscope speculum to be combined with an otoscope for use in easily and reliably diagnosing inner ear conditions. More specifically, the otoscope speculum can include a body having a neck and a stopper portion, a cap having a flange overhand and a flat distal face, a channel having a proximal opening in the cap and a distal opening in the neck, and at least one light embedded within the neck. Therefore, when the otoscope speculum is inserted into an car, the interior of the car can be illuminated, and potential inner ear conditions can be more easily identified. By embedding the light into the neck, light can more easily illuminate the interior ear compared to traditional methods where the light is directed down the channel from the otoscope itself.

Figure 2:
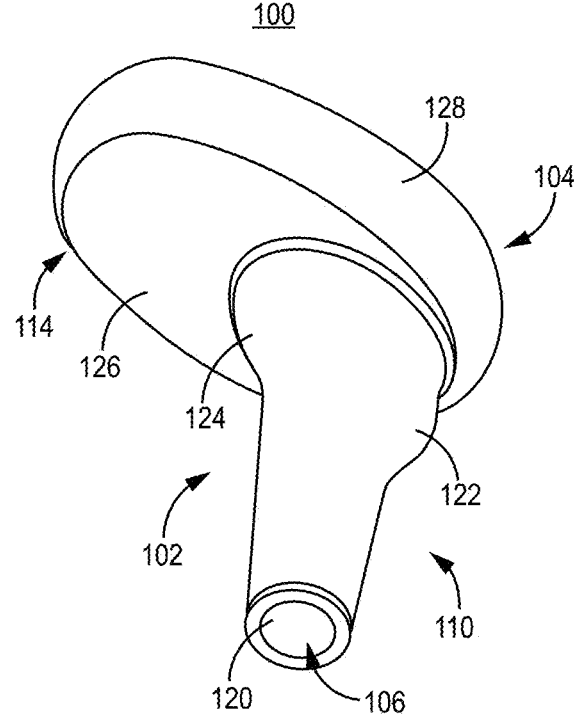
FIG. 2 is a bottom perspective view of the otoscope speculum.
Figures 3, 4:
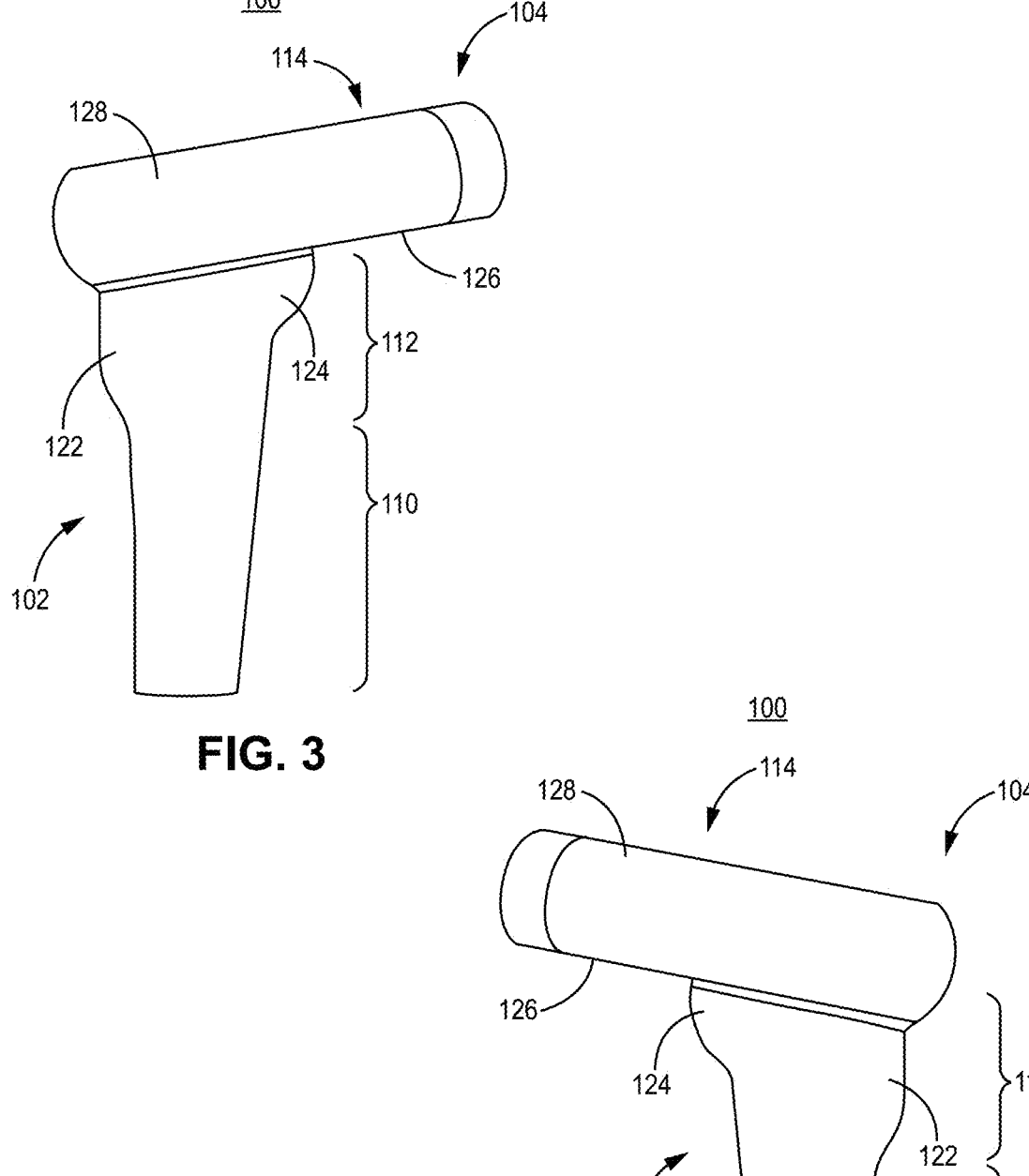
FIG. 3 is a left side view of the otoscope speculum.
FIG. 4 is a right side view of the otoscope speculum.
Figure 7:
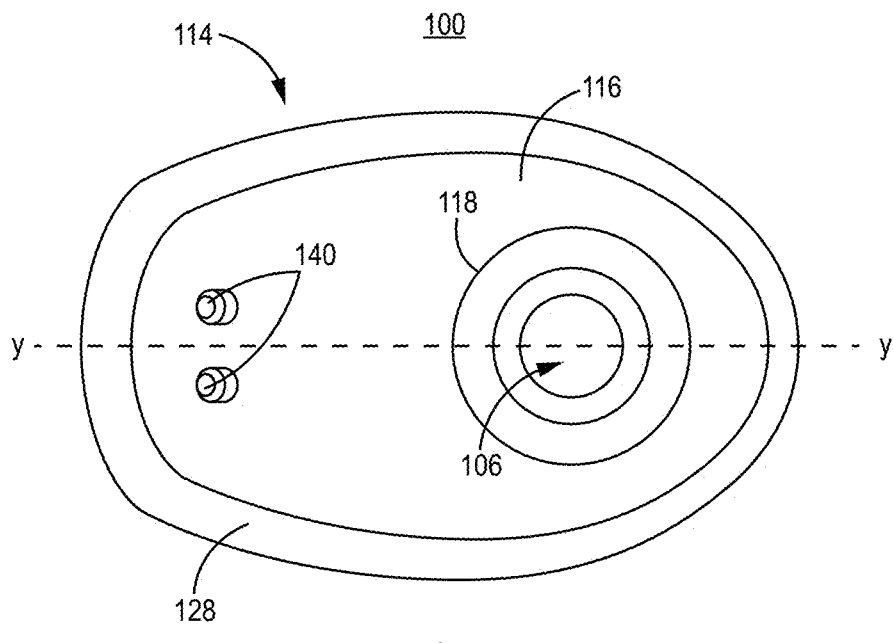
FIG. 7 is a top view of the otoscope speculum.
Figure 8:
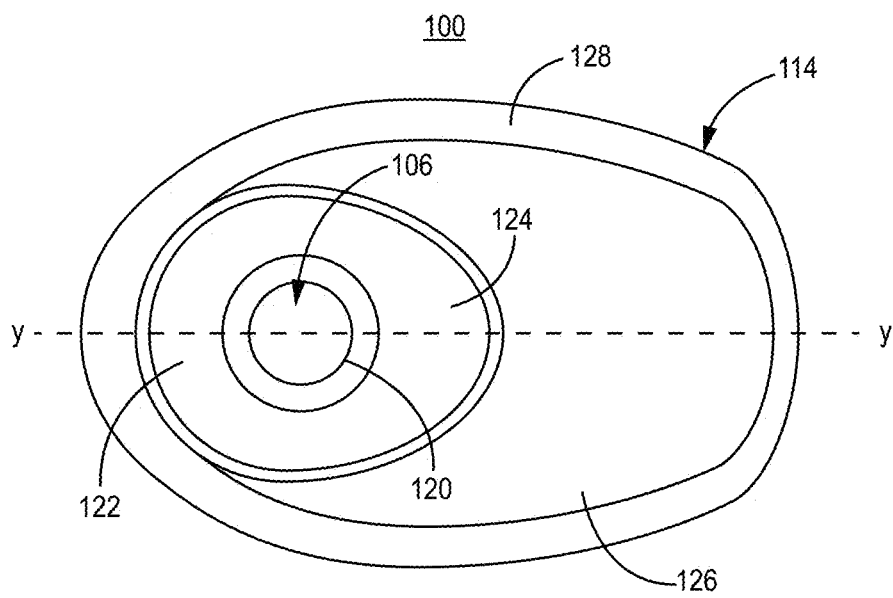
FIG. 8 is a bottom view of the otoscope speculum.
Figure 9:
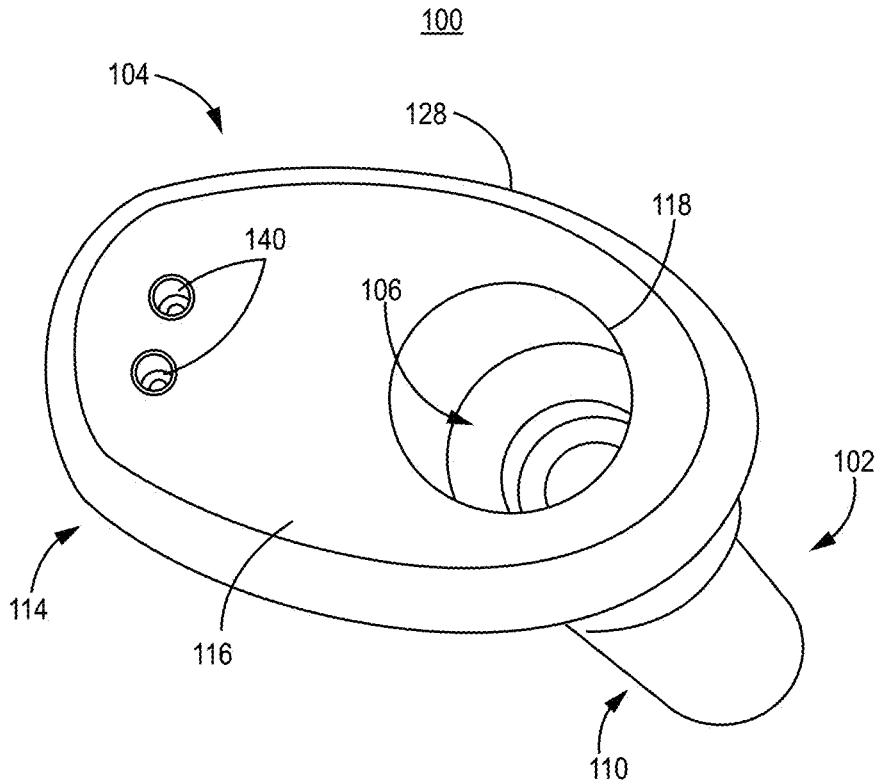
FIG. 9 is a top perspective view of the otoscope speculum.
Figure 10:
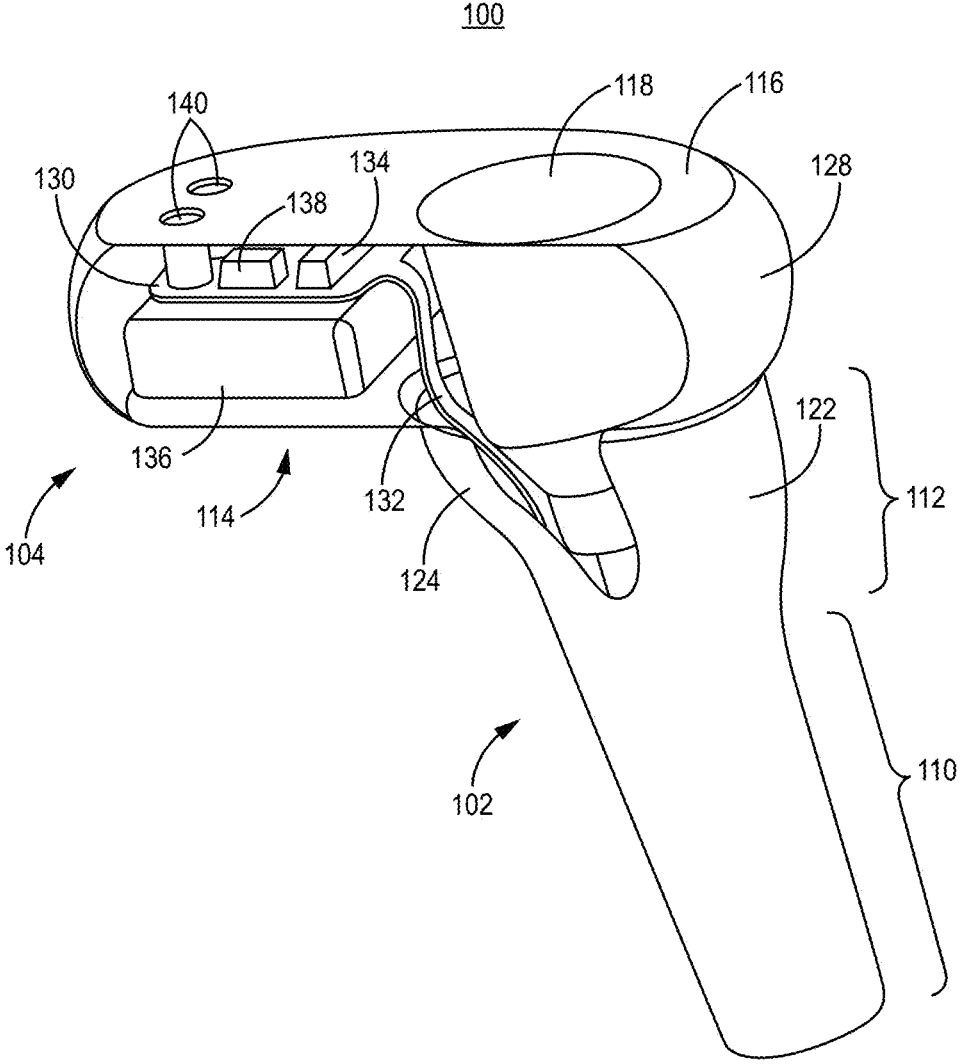
FIG. 10 is a cross-sectional view of the otoscope speculum taken from line 10-10 in FIG. 5.
Figure 11:
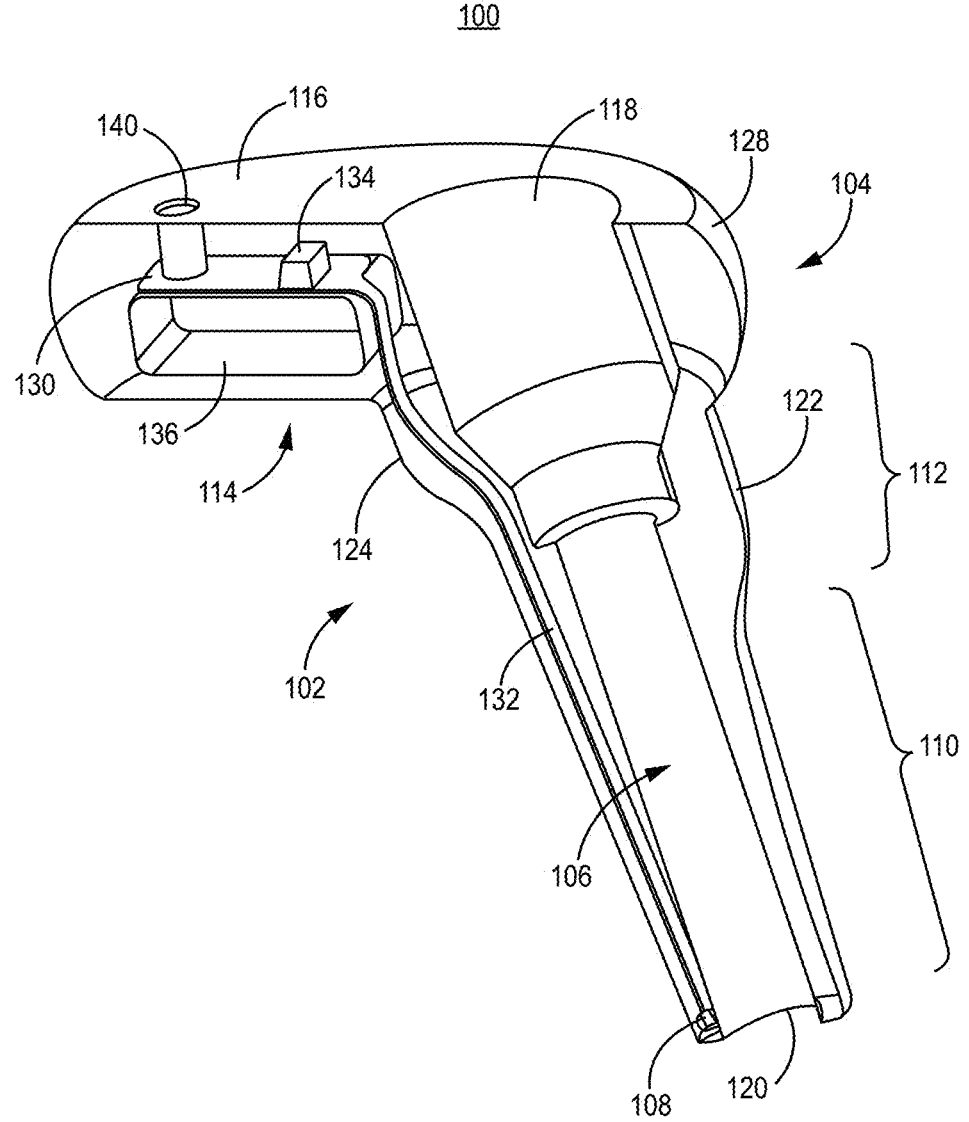
FIG. 11 is a cross-sectional view of the otoscope speculum taken from line 11-11 in FIG. 5.

FIGS. 1-11 illustrate various views of an example of an otoscope speculum according to the present disclosure. FIG. 1 is a side perspective view of an otoscope speculum. FIG. 2 is a bottom perspective view of the otoscope speculum. FIG. 3 is a left side view of the otoscope speculum. FIG. 4 is a right side view of the otoscope speculum. FIG. 5 is a front view of the otoscope speculum. FIG. 6 is a rear view of the otoscope speculum. FIG. 7 is a top view of the otoscope speculum. FIG. 8 is a bottom view of the otoscope speculum. FIG. 9 is a top perspective view of the otoscope speculum. FIG. 10 is a cross-sectional view of the otoscope speculum taken from line 10-10 in FIG. 5. FIG. 11 is a cross-sectional view of the otoscope speculum taken from line 11-1 in FIG. 5.

Generally, the otoscope speculum has roughly cylindrical body with an oblong disc-shaped cap. Therefore, in some embodiments, the otoscope speculum can include a body having an approximately cylindrical neck and a stopper portion, and can further include a cap having a flange overhang and a flat distal face. The length of the body and the height of the cap can be defined by a first vertical axis (for example, axis x in FIG. 6), and the length of the cap can be defined by a second, approximately perpendicular axis (for example, axis y in FIG. 7). The otoscope speculum can further have a channel with a proximal opening in the cap and a distal opening in the neck, thereby enabling a user to see from one end of the otoscope speculum out through the other end. As mentioned above, to illuminate the ear when the otoscope speculum is inserted, the neck can include at least one embedded light. The body and the cap can both be comprised of the same or different flexible and/or malleable material(s) (such as, but not limited to, polymers, rubbers, etc.) or they can be comprised of a combination of materials. For example, the body and the cap can be comprised of silicone. In some cases, the material can be clear/transparent where at least the embedded light is located to enable the light to illuminate into the car from its embedded position in the otoscope speculum. In other cases, the entire body, the entire cap or both can be transparent.

While the term "connect" is used herein to describe components adjacent to each other, construction of the otoscope speculum may be such that the entire speculum is molded as one piece. Therefore, the term connect may mean a physical connection between two components (such as with a screw, nail, or adhesive) or that two components are adjacent each other and inseparable.

As illustrated in FIG. 1, otoscope speculum 100 can be comprised of body 102 having neck 110 adjacent to stopper portion 112, cap 104 having flange overhang 114 and flat, proximal top face 116, channel 106 having proximal opening 118 in cap 104 and distal opening 120 in neck 110, and at least one light 108 embedded within neck 110. Generally, the left and right halves of otoscope speculum 100, separated by axis y in FIGS. 7-8, may be symmetrical, as illustrated in FIGS. 7-8, such that each side is equal in length and mirrors the other. More specifically, body 102, cap 104, and/or channel 106 may be symmetrical with the sides mirroring each other while some of the interior mechanics, as illustrated in FIGS. 10-11, may or may not be symmetrical.

As mentioned above, body 102 can be approximately cylindrical. More specifically, body 102 can include cylindrical neck 110, which can be the cylindrical portion, and stopper portion 112. Neck 110 may be uniform in circumference, or it may be wider at one end compared to the other. For example, as illustrated in FIGS. 3-4, neck 110 narrows slightly from its proximal end near stopper portion 112 to its distal end. However, neck 110 may narrow the opposite direction as well: from its distal end to its proximal end near stopper portion 112.

In some embodiments, neck 110 may connect directly to cap 104. However, as illustrated herein, neck 110 may transition into stopper portion 112, and stopper portion 112 can connect to cap 104. The stopper portion is structured and configured to assist a user with aligning the otoscope speculum precisely in an ear to maximize the user's view of the interior of the ear. More specifically, as illustrated in FIGS. 3-4, stopper portion 112 can have anterior protrusion/bump 122 and posterior protrusion/bump 124. The protrusions/bumps 122, 124 are a widening of body 102 to aid in aligning otoscope speculum 100 in an car and to prevent otoscope speculum 100 from inserting more than a predetermined distance (i.e., the height/length of the neck) into an car. In some embodiments, anterior protrusion 122 can have a larger/longer height than posterior protrusion 124 such that it aligns with common car anatomy. Therefore, body 102 may be widest at its proximal end, where both anterior protrusion 122 and posterior protrusion 124 are located, narrowest at its distal end, wherein distal opening 120 is located, and may have an intermediate width at the distal portion of stopper portion 112, wherein anterior protrusion 122 is present and posterior protrusion 124 is not present.

While body 102 may have a gradual shape change between its proximal and distal ends, cap 104 may be more geometrical. In some embodiments, cap 104 can be approximately cylindrical (for example, an oblong disc-like shape, wherein the height of the cap can be less than the length of the cap), as illustrated in FIGS. 7-8, with flat, proximal top face 116, flat, proximal bottom face 126, and rounded sides 128. The top and bottom faces 116, 126 can be roughly oval in shape, with a rounded, ovular posterior end and an arced anterior end having defined, angular end points. In addition to top and bottom faces 116, 126 and rounded sides 128, cap 104 can be comprised of flange overhang 114, as illustrated in FIGS. 1-4.

Flange overhang 114 can be located on the posterior end of otoscope speculum 100 and can be structured and configured to fit within the concha cavum of the outer car. As mentioned above, cap 104 has top and bottom faces 116, 126. In some embodiments, at least a portion of top and bottom faces 116, 126 are located in flange overhang 114. More specifically, the arced, anterior end of top and bottom faces 116, 126 may be located in the same region of cap 104 as flange overhang 114. In some embodiments, flange overhang 114 may have a similar width to that of posterior protrusion 122 of stopper portion 112. Therefore, approximately one half of bottom face 126 may be attributed to flange overhang 114 while an approximate second half of bottom face 126 may be connected to posterior protrusion 122, as illustrated in FIGS. 2-4.

In addition to body 102 and cap 104, otoscope speculum 100 can include channel 106. As mentioned above, and illustrated in FIGS. 7-8, the channel can penetrate completely from a proximal end of the otoscope speculum through to the distal end of the otoscope speculum. More specifically, channel 106 can have proximal opening 118 in cap 104 and distal opening 120 at the distal end of neck 110.

Channel 106 can be tube-shaped to align with the geometry of body 102. In some embodiments, the channel has a uniform diameter along its entire length. In other embodiments, as illustrated in FIGS. 7, 9 and 11, channel 106 may have varying diameters along its length.

As mentioned above, the otoscope speculum can be combined with an otoscope to view and diagnose conditions of the inner ear. Therefore, to pair with the otoscope, proximal opening 118 in cap 104 of otoscope speculum 100 may be wider than at least another portion of channel 106. More specifically, channel 106 may have a larger diameter near its proximal end compared to its distal end. For example, the portion of channel 106 located in cap 104 may be the portion with the largest diameter, while the portion of channel 106 located at a distal end of neck 110 may be the portion with the narrowest diameter. In some embodiments, there are other, varying diameters between those two ends. For example, as illustrated in FIG. 11, channel 106 may have a first, broadest part at the proximal end of otoscope speculum 100 within cap 104, may narrow along a beveled slope within posterior protrusion 124 into a second part where the second part may span portions of posterior protrusion 124 and anterior protrusion 122, and may narrow again into a third part below posterior protrusion 124. While this specific embodiment of channel 106 is illustrated in the figures and disclosed herein, it is envisioned that other channel forms may be taken. For example, one or more of the three cylindrical portions may not be present, the beveled slope may not be present, and/or the locations where the transitions between parts happen may be adjusted to other locations along the x axis.

The structural features of body 102, cap 104, and channel 106, as described above, enable an otoscope to pair with otoscope speculum 100 and further enable otoscope speculum 100 to be securely and reliable inserted into an ear such that the otoscope is positioned to maximize a user's sightline into the ear. However, because insertion of an object into an ear typically blocks most, if not all, ambient light, artificial illumination is needed to see the details of the ear. Therefore, otoscope speculum 100 includes at least one embedded light 108.

In some embodiments, embedded light 108 can be completely embedded within otoscope speculum 100, as illustrated in FIG. 11. Therefore, in some cases, no portion of light 108 is located on an exterior surface of otoscope speculum 100; it can be completely encased by the material forming body 102 and/or cap 104, as illustrated in FIGS. 1-2, 8 and 11.

Regarding the positioning and structure of light 108, in some embodiments, light 108 may be completely embedded near the distal tip of neck 110, as illustrated in FIG. 11. Alternatively, light 108 may be embedded closer to cap 104, such as near proximal end of neck 110, in the walls of stopper portion 112, or even within cap 104. Light 108 may be comprised of one or more illuminating components. These illuminating components may be positioned adjacent each other, may be (in the cases of two or more components) equally spaced apart, or may be at random intervals relative to each other. For example, light 108 may be comprised of two light emitting diodes (LEDs) that are positioned adjacent each other near the distal tip of neck 110. Alternatively, the two LEDs may be positioned at opposite locations along a circumference of neck 110 such that they are equidistant from each other, or they may be positioned at random intervals with different distances between their two connecting distances. In another example, light 108 may be comprised of at least four LEDs that are positioned circumferentially around the distal tip of neck 110. The at least four LEDs may be equally or randomly spaced apart from one another. In yet another example, light 108 may be comprised of a fiber optic cable or a light pipe, wherein the fiber optic cable/light pipe has an emitting end near the distal tip of neck 110.

In some embodiments, light 108 may be located on a posterior portion of neck 110, as illustrated in FIG. 11. This may aid with more easily connecting to a power source in flange overhang 114, which is also on a posterior portion of otoscope speculum 100. However, light 108 in not required to be on a posterior portion of neck 110 and could, instead, be located on an anterior portion or on a side. To direct light into an appropriate portion of the ear canal so as to maximize illumination within the ear, light 108 may be aligned between a parallel position to axis x and a 30-degree angle toward a central axis of the channel. In some embodiments, regardless of orientation or location, light 108 may have a built-in lens having a beam range of up to 120 degrees (for example, between 45-60 degrees).

As illustrated in FIG. 11, the diameter of channel 106 may be narrower than the diameter of neck 110 and stopper portion 112 to enable electronics such as wiring and lighting to be embedded within the walls of otoscope speculum 100. This enables light 108 to be located at a distance from a power source. For example, light 108 can be located at distal tip of neck 110 while a power source can be located in flange overhang 114, as illustrated in FIG. 11.

In some embodiments, light 108 can be connected to circuit board 130 (for example, via connector 132) that is embedded within otoscope speculum 100 (for example, within flange overhang 114 of cap 104). Circuit board 130 can have a flat top and bottom face that is parallel to top and bottom faces 116, 126 of cap 104. Further, circuit board 130 can include switch 134, such as a reed or a hall effect switch (located on a top surface, as illustrated in FIGS. 10-11), that aids in activating light 108. In some cases, switch 134 can be activated by a component in channel 106. Alternatively, when otoscope speculum 100 is paired with an otoscope, presence of the otoscope within channel 106 may activate switch 134, which can activate light 108. For example, a magnet may be embedded into a component of the otoscope speculum that protrudes slightly into the channel (such as a living hinge or spring-loaded paddle) such that when otoscope is inserted into the channel, it physically moves the magnet closer to the switch and causes the switch to establish an "on" configuration. Thereafter, when the otoscope is removed from the otoscope speculum, the hinge/paddle can revert back to its location within the channel and the switch can automatically revert to an "off" configuration due to the magnet moving away and back into the channel. In another example, the switch may be included in the otoscope itself, such that the otoscope speculum is activated by the otoscope switch when the otoscope and otoscope speculum come into contact with each other. More specifically, a magnet can be added to a predetermined location on the otoscope speculum and when the switch of the otoscope is aligned appropriately with the magnet, such that the otoscope and otoscope speculum are properly aligned with each other, the light can be activated.

To enable the circuit board to activate the at least one light, the circuit board may interface with a power source. More specifically, circuit board 130 may interface with battery 136. As illustrated in FIGS. 10-11, battery 136 can be embedded within flange overhang 114 of cap 104 and circuit board 130 may be positioned on a top surface of battery 136. Further, circuit board 130 may include a current limiting diode 138 positioned on a top face of circuit board 130. In some embodiments, flange overhang 114 may also include two small holes 140, which lead from top face 116 down into circuit board 130, as illustrated in FIGS. 10-11, and interface with battery charging electrodes (not illustrated). Therefore, battery 136 may be positioned near the bottom face 126 of cap 104 and inside flange overhang 114, circuit board 130 may be positioned on top of battery 136 and also within flange overhang 114, circuit board 130 may connect to light 108 via connector 132, switch 134 and current limiting diode 138 may be positioned on a top portion of circuit board 130 and inside flange overhang 114, and holes 140 may connect circuit board 130 to top face 116 of cap 104.

The various embodiments described above are provided by way of illustration only and should not be construed to limit the claims attached hereto. Those skilled in the art will readily recognize various modifications and changes that may be made without following the example embodiments and applications illustrated and described herein and without departing from the true spirit and scope of the following claims.

What is claimed is:

1. An otoscope speculum comprising:
a body having a neck and a stopper portion, the stopper portion comprising an anterior bump and a posterior bump configured to aid in aligning the otoscope speculum in an ear, wherein a length of the body is defined by a first axis, and wherein the posterior bump has a shorter height in a direction along the length than height of the anterior bump;
a cap having a flange overhang and a flat distal face, wherein a length of the cap is defined by a second axis and a height of the cap is defined by the first axis;
a channel having a proximal opening in the cap and a distal opening in the neck;
at least one light embedded within the neck.

2. The otoscope speculum of claim 1, wherein the at least one light is completely embedded near the distal tip of the neck.

3. The otoscope speculum of claim 2, wherein the at least one light is comprised of two light emitting diodes positioned adjacent to each other.

4. The otoscope speculum of claim 3, wherein the two light emitting diodes are located on a posterior portion of the neck.

5. The otoscope speculum of claim 2, wherein the at least one light is aligned between a parallel position to the first axis of the body and a 30-degree angle toward a central axis of the channel.

6. The otoscope speculum of claim 2, wherein the at least one light is either a fiber optic cable or a light pipe, and wherein the at least one light has an emitting end near the distal tip of the neck.

7. The otoscope speculum of claim 1, wherein the neck is approximately cylindrical.

8. The otoscope speculum of claim 1, wherein the anterior bump extends along the length closer to the distal opening in the neck than the posterior bump.

9. The otoscope speculum of claim 1, wherein the body and the cap are comprised of a transparent silicone.

10. The otoscope speculum of claim 1, wherein the at least one light is connected to a circuit board that is embedded within the otoscope speculum.

11. The otoscope speculum of claim 10, wherein the circuit board is embedded within the flange of the cap.

12. The otoscope speculum of claim 11, wherein the circuit board includes a switch.

13. The otoscope speculum of claim 12, wherein the switch is one of a reed or hall effect switch.

14. The otoscope speculum of claim 13, wherein the switch is activatable by a component in the channel.

15. The otoscope speculum of claim 13, wherein the circuit board interfaces with a battery.

16. The otoscope speculum of claim 15, wherein the battery is embedded within the flange of the cap.

17. The otoscope speculum of claim 16, wherein the circuit board further includes a current limiting diode.

18. The otoscope speculum of claim 1, wherein
the cap is approximately cylindrical, and
the height of the cap is less than the length of the cap.

19. The otoscope speculum of claim 1, wherein the at least one light having a beam range of up to 120 degrees.

20. The otoscope speculum of claim 19, wherein the beam range is 45-60 degrees.

21. The otoscope of claim 1, wherein the neck extends at a skewed angle relative to the flat distal face of the cap.

* * * * *